United States Patent
Gómez et al.

(10) Patent No.: US 9,908,896 B2
(45) Date of Patent: Mar. 6, 2018

(54) P38 AND JNK MAPK INHIBITORS FOR THE TREATMENT AND PROPHYLAXIS OF DEGENERATIVE DISEASES OF THE NERVOUS SYSTEM

(71) Applicant: ALLINKY BIOPHARMA, Madrid (ES)

(72) Inventors: Patricia Gómez, Madrid (ES); Esther Carrasco, Madrid (ES); Pedro Campos, Madrid (ES); Miguel Vega, Madrid (ES); Juan Jesús Gómez-Reino, Madrid (ES); Juan Jesús Pérez, Madrid (ES); Ángel Messeguer, Madrid (ES); Ignacio Torres, Madrid (ES)

(73) Assignee: ALLINKY BIOPHARMA, Madrid (ES)

( * ) Notice: Subject to any disclaimer, the term of this patent is extended or adjusted under 35 U.S.C. 154(b) by 0 days.

(21) Appl. No.: 15/317,832

(22) PCT Filed: Jun. 16, 2015

(86) PCT No.: PCT/EP2015/063419
§ 371 (c)(1),
(2) Date: Dec. 9, 2016

(87) PCT Pub. No.: WO2015/193281
PCT Pub. Date: Dec. 23, 2015

(65) Prior Publication Data
US 2017/0107230 A1    Apr. 20, 2017

(30) Foreign Application Priority Data

Jun. 16, 2014   (EP) .................................... 14382231

(51) Int. Cl.
*C07D 498/04*    (2006.01)

(52) U.S. Cl.
CPC .................................. *C07D 498/04* (2013.01)

(58) Field of Classification Search
CPC ...................................................... C07D 498/04
USPC ............................................................ 544/305
See application file for complete search history.

(56) References Cited

FOREIGN PATENT DOCUMENTS

| WO | 2008/028860 A1 | 3/2008 |
|----|----------------|--------|
| WO | 2014/094816 A1 | 6/2014 |

OTHER PUBLICATIONS

International Search Report and Written Opinion for International Patent Application No. PCT/EP2015/063419, dated Oct. 8, 2015, 11 pages.
International Preliminary Report on Patentability for International Patent Application No. PCT/EP2015/063419, dated May 23, 2016 18 pages.

*Primary Examiner* — Kahsay Habte
(74) *Attorney, Agent, or Firm* — Merchant & Gould P.C.

(57) ABSTRACT p38 and JNK mitogen activated protein (MAP) kinase al losteric inhibitors are useful for treatment and/or prophylaxis of degenerative diseases of the nervous system. Compounds are used in a method for treatment and/or prophylaxis of the diseases and for use in therapy in general. The compounds bind to the region composed of amino acids at positions 170-199 of Mitogen-activated protein kinase 14 (Uniprot accession nr Q16539 or SEQ ID No 1) and/or Mitogen-activated protein kinase 11 (Uniprot accession nr Q15759 or SEQ ID No 2), SEQ ID NO.1 and SEQ ID NO.2 being the amino acid sequences of MAPK14 (p38α) and MAPK11 (p38β), respectively. The specific region composed of amino acids at positions 170-199 is herein disclosed as SEQ ID HO.4 for Mitogen-activated protein kinase 14 and SEQ ID NO.5 for Mitogen-activated protein kinase 11 and are believed to be new inhibitory binding sites.

11 Claims, 2 Drawing Sheets

P38 AND JNK MAPK INHIBITORS FOR THE TREATMENT AND PROPHYLAXIS OF DEGENERATIVE DISEASES OF THE NERVOUS SYSTEM

This application is a National Stage Application of International Patent Application No. PCT/EP2015/063419, filed 16 Jun. 2015, which claims benefit of Serial No. 14382231.0, filed 16 Jun. 2014 in Europe and which applications are incorporated herein by reference. To the extent appropriate, a claim of priority is made to each of the above disclosed applications.

FIELD OF THE INVENTION

The present invention provides new p38 and JNK mitogen activated protein kinase (MAPK) allosteric inhibitors which are useful for the treatment and prophylaxis of degenerative diseases of the nervous system. Examples of such diseases include Parkinson's disease, Alzheimer's disease, retinitis pigmentosa, age-related macular degeneration and dementia,

BACKGROUND ART p38α MAP kinase (MAPK) is an intracellular serine/threonine kinase involved in the regulation of inflammatory cell signals and plays a central role in the regulation of pro-inflammatory cytokine production. Activation of p38α is produced by upstream kinases MKK6 and MKK3. At molecular level, like other protein kinases, p38α is responsible for the transfer of the γ-phosphate form ATP to a range of substrate proteins including the transcription factors ATF2, Elk-1 and MEF2A and downstream kinases like MK2, MK3, PRAK, MNK1/2 and MSK1, modulating their function (Stokoe et al., 1992, EMBO J. 11, 3985-3994).

p38α has been identified as a potential target for anti-inflammatory drugs, and different binding sites for these drugs have been identified (Akella et al., January 2008, Biochim Biophys Acta; 1784(1): 48-55). Yong et al. review different p38 MAPK inhibitors which are under development as potential drugs for the treatment of inflammatory diseases and cancer (Yong et al., 2009, Expert Opin. Investig. Drugs; 18(12)). The majority of the drug candidates have proved to be competitive with ATP, binding to the active site. A few inhibitors have also been found that bind to a site adjacent to the active site. Akella et al. discuss the potential relevance of other binding sites such as the binding sites for D-motifs, FXFP and the Backside site.

Recently, evidences from both clinical studies and preclinical animal models have implicated overproduction of proinflammatory cytokines as a contributor to pathophysiology progression in chronic neurodegenerative disorders like Alzheimer's disease, Parkinson's disease and multiple sclerosis (e.g. A. D. Bachstetter et al., Ageing and Disease 2010, Vol. 1, No. 3, pp. 199-211). This indicates that p38 MAPK signalling pathways could be viable targets for modulating inflammatory responses in neurological diseases.

Other MAP kinase that is also an important pharmaceutical target in the treatment of degenerative diseases of nervous system is the JNK MAP kinase. JNK MAP kinase provides key signals in the brain for both neuronal apoptosis and amyloidigenic processing of APP, the two most important characteristics of Alzheimer's disease.

Despite several p38 MAPK inhibitors have been reported, they are currently no studies on use of p38 and JNK MAPK inhibitors for the treatment of degenerative diseases of nervous system or not even information available on whether any of such compounds are capable of passing through the blood-brain barrier.

SUMMARY OF THE INVENTION

Accordingly, the object underlying the present invention is to provide compounds, in particular, p38 and JNK MAPK inhibitors as well as compositions and formulations thereof that are useful for the treatment and/or prophylaxis of degenerative diseases of the nervous system. The term "degenerative diseases of the nervous system" as used herein refers to a group of disorders in which there is gradual, generally symmetric, relentlessly progressive wasting away of neurons. Typically, the degenerative diseases of the nervous system begin insidiously and run a gradually progressive course which may extend over many years. A common feature of these diseases is a nearly selective involvement of anatomically or physiologically related systems of neurons.

A common way of classifying various degenerative diseases of nervous system is based on grouping them according to the clinical features that may be found in an actual case. Thus, one group of said diseases include syndromes in which progressive dementia is an outstanding feature in the absence of other prominent neurologic signs. This group of degenerative diseases comprises inter ilia senile dementia and Alzheimer's disease which both involve diffuse cerebral atrophy. A further example of this group is the Pick's disease involving circumscribed cerebral atrophy.

A further important group of degenerative diseases of the nervous system are syndromes in which progressive dementia is combined with other neurologic signs. Examples of such disorders are, for instance, Huntington's chorea and cerebrocerebellar degenerations which occur principally in adults. A further subgroup of examples of said disorders occur both in children and adults and include inter alia amaurotic family idiocy (neuronal lipidoses), leukodystrophy, familial myoclonus epilepsy, Hallervorden-Spatz disease and Wilson's disease (hepatolenticular degeneration, Westphal-Strumpell pseudosclerosis).

A further important group of degenerative diseases of the nervous system are syndromes chiefly manifested by gradual development of abnormalities of posture of involuntary movements. This group of disorders includes paralysis agitans (Parkinson's disease), dystonia musculorum deformans (torsion dystonia), Hallervorden-Spatz disease and other restricted dyskinesias, familial tremor and spasmodic torticollis.

A further important group of degenerative diseases of the nervous system are syndromes chiefly manifested by slowly developing ataxia. These disorders include but are not limited to cerebellar degenerations and spinocerebellar degenerations (Friedrich's ataxia, Marie's hereditary ataxia) etc.

A further group of degenerative diseases of the nervous system includes syndromes with slowly developing muscular weakness and wasting. The corresponding disorders may proceed without sensory changes such as, for instance, amyotrophic lateral sclerosis (ALS), progressive muscular atrophy, cachexia, sarcopenia, progressive bulbar palsy, or primary lateral sclerosis in adults or disorders such as infantile muscular atrophy (Werdnig-Hoffmann disease), diverse forms of familial progressive muscular atrophy (including Wohlfart-Kugelberg-Welander syndrome) or hereditary spastic paraplegia in children or young adults.

Said group of diseases further includes those with sensory changes such as progressive neural muscular atrophy, e.g. peroneal muscular atrophy (Charcot-Marie-Tooth) and hypertrophic interstitial neuropathy (Dejerine-Sottas) or miscellaneous forms of chronic progressive neuropathy.

Finally, a further group of degenerative diseases of the nervous system are syndromes chiefly manifested by progressive visual loss. These disorders include inter alia hereditary optic atrophy (Leber's disease), age-related macular degeneration and pigmentary degeneration of the retina (retinitis pigmentosa).

The present invention further provides compounds for use in a method for treatment and/or prophylaxis of degenerative diseases of the nervous system and associated diseases. Preferably, the compound of the present invention is capable of binding to the region composed of amino acids at positions 170-199 of Mitogen-activated protein kinase 14 (Uniprot accession nr Q16539 or SEQ ID No 1) and/or Mitogen-activated protein kinase 11 (Uniprot accession nr Q15759 or SEQ ID No 2), SEQ ID NO.1 and SEQ ID NO.2 being the amino acid sequences of MAPK14(p38α) and MAPK11 (p38β), respectively. The specific region composed of amino acids at positions 170-199 is herein disclosed as SEQ ID NO.4 for Mitogen-activated protein kinase 14 and SEQ ID NO.5 for Mitogen-activated protein kinase 11 and are believed to be new inhibitory binding sites. Its three-dimensional structure is available from the Protein Data Bank (PDB entry 2OZ,A).

Importantly, the compounds of the present invention not only act as efficient p38 and JNK MAPK inhibitors but also possess excellent blood-brain barrier permeability. Accordingly, administration of compounds of the present invention to a patient leads to a considerable accumulation of said compounds in the brain and nervous system tissues of the patient. This enables interaction of said compounds with p38 and JNK MAPK in the corresponding tissues and allows an efficient treatment and/or prophylaxis of degenerative diseases of the nervous system.

In particular, the present invention provides compounds of the general Formula (I):

(I)

or a salt thereof, wherein

A is a polycyclic aromatic, heteroaromatic, alicyclic, heteroalicyclic substituent or is represented by the following structure:

$R^1$ is a hydrogen atom, a halogen atom or a $C_{1-6}$-alkyl group optionally substituted with one or more halogen atoms, $R^2$ is a $C_{1-6}$-aliphatic group optionally substituted with one or more halogen atoms, X is represented by —O—, —S—, —S(O)—, —S(O)$_2$—, —NH—, —C(O)—, or —CH$_2$—, $Y^1$, $Z^1$, $Y^2$, $Z^2$ and $Y^3$ are independently represented by —CH— or —N—, and W is represented by —O—, —S—, —NH—, or —C(O)—; and wherein the polycyclic aromatic, heteroaromatic, alicyclic, heteroalicyclic substituent can be optionally substituted by —W—$R^2$.

The present invention also provides methods of treatment and/or prophylaxis using the p38 and JNK MAPK inhibitors described herein for the treatment and/or prophylaxis of degenerative diseases of the nervous system.

In a further aspect, the present invention relates to a pharmaceutical composition comprising a therapeutically effective amount of the compound of the general Formula (I) or a salt thereof as active ingredient. The pharmaceutical composition of the present invention is preferably formulated as an oral dosage form to allow its convenient administration to the patient.

A further aspect of the present invention is the compound of the general Formula (I) for use in the treatment of a human or animal body, in particular for use in the treatment and/or prophylaxis of degenerative diseases of the nervous system. In other words, the present invention provides methods of treatment using the p38 and JNK MAPK inhibitors described herein for the treatment of a human or animal body, in particular a method for the treatment of degenerative diseases of nervous system.

DETAILED DESCRIPTION

The present invention provides compounds for use in therapy and/or prophylaxis of degenerative diseases of the nervous system, in particular to p38 and JNK mediated neurodegenerative diseases. The compounds of the present invention are capable of passing the blood-brain barrier and bind to the region composed of amino acids at positions 170-199 of SEQ ID NO.1 and/or SEQ ID NO.2, SEQ ID NO.1 and SEQ ID NO.2 being the amino acid sequences of MAPK14(p38α) and MAPK11(p38β), respectively. The compounds of the present invention have preferably an inhibitory effect on the protein of SEQ ID NO.1 and/or SEQ ID NO.2, but not on the mutant R186A or R189A of the protein of SEQ ID NO.1 and/or SEQ ID NO.2.

One aspect of the present invention relates to the compound of general Formula (I)

(I)

or a salt thereof, wherein

A is a polycyclic aromatic, heteroaromatic, alicyclic, heteroalicyclic substituent or is represented by the following structure:

$R^1$ is a hydrogen atom, a halogen atom or a $C_{1-6}$-alkyl group optionally substituted with one or more halogen atoms, $R^2$ is a $C_{1-6}$-aliphatic group optionally substituted with one or more halogen atoms, X is represented by —O—, —S—, —S(O)$_2$—, —NH—, —C(O)—, or —CH$_2$—, $Y^1$, $Z^1$, $Y^2$, $Z^2$ and $Y^3$ are independently represented by —CH— or —N—, and W is represented by —O—, —S—, —NH—, or —C(O)—; and wherein the polycyclic aromatic, heteroaromatic, alicyclic, heteroalicyclic substituent can be optionally substituted by —W—$R^2$.

Preferably, polycyclic aromatic, heteroaromatic, alicyclic, heteroalicyclic substituents are fused bicyclic aromatic, heteroaromatic, alicyclic, heteroalicyclic substituents.

As used herein the term "polycyclic aromatic substituent" may refer to a group selected from naphthyl, anthracenyl, phenanthryl and tetrahydronaphthyl groups.

The term "polycyclic heteroaromatic substituent" may refer to a group selected from indanyl, indenyl, quinolyl, isoquinolyl, 1,2,3,4-tetrahydroquinolyl, 1,2,3,4-tetrahydroisoquinolyl, benzimidazolyl, benzofuryl, benzothienyl, dihydrobenzofuranyl, dihydrobenzothienyl and benzisoxazolyl.

According to the present invention, the term "polycyclic alicyclic substituent" may refer to a group such, as norbornyl, 1-adamantyl, 2-adamantyl, isobornyl, or decahydronaphthyl.

Finally, the term "polycyclic heterocyclic substituent" may refer to decahydroquinolyl, decahydroisoquinolyl, octahydroquinolyl, octahydroisoquinolyl or quinuclidinyl groups.

In some preferred embodiment of the present invention, the substituent A is represented by one of the following structures:

In yet a further preferred embodiment, the compounds of the present invention are represented by the general Formula (II):

(II)

or a salt thereof, wherein $R^1$ is a hydrogen atom, a halogen atom or a $C_{1-6}$-alkyl group optionally substituted with one or more halogen atoms, $R^2$ is a $C_{1-6}$-aliphatic group optionally substituted with one or more halogen atoms, X is represented by —O—, —S—, —S(O)—, —S(O)$_2$—, —NH—, —C(O)—, or —CH$_2$—, $Y^1$, $Z^1$, $Y^2$, $Z^2$ and $Y^3$ are independently represented by —CH— or —N—, and W is represented by —O—, —S—, —NH—, or —C(O)—.

In the present application, the term "a halogen atom" may refer to a fluorine atom, a chlorine atom, a bromine atom or an iodine atom, a fluorine or a chlorine atom being particularly preferred. In a particularly preferred embodiment the term "a halogen atom" refers to a fluorine atom.

The term "aliphatic group" as used herein may refer to a straight chain or branched alkyl group, a cycloalkyl group, an alkylcyclo-alkyl group, a cycloalkylalkyl group, an alkenyl group, an alkyl group, an alkadienyl group or an alkynenyl group. The aliphatic group may be saturated or contain one or several carbon-carbon double and/or triple bonds. Accordingly, the term "$C_{1-6}$-aliphatic group" encompasses $C_{1-6}$-alkyl groups, $C_{3-6}$-cycloalkyl groups, $C_{4-6}$-alkylcycloalkyl groups, $C_{4-6}$ cycloalkylalkyl groups, $C_{2-6}$-alkenyl groups, $C_{2-6}$-alkynyl groups, $C_{4-6}$-alkadienyl groups and $C_{4-6}$-alkynenyl groups. Preferably, the term "$C_{1-6}$-aliphatic group" refers to a $C_{1-6}$-alkyl group.

The term "alkyl group" refers to straight chain or branched alkyl group. Thus, the term "$C_{1-6}$-alkyl group" refers to straight chain or branched alkyl group having between 1 and 6 carbon atoms. Examples of $C_{1-6}$-alkyl groups include are not limited to methyl, ethyl, n-propyl, i-propyl, n-butyl, i-butyl, tert.-butyl, n-pentyl and n-hexyl groups. In one preferred embodiment of the present invention, "$C_{1-6}$-alkyl group" is a straight chain or branched alkyl group having one to four carbon atoms. In a particularly preferred embodiment, the "$C_{1-6}$-alkyl group" is methyl, ethyl or n-propyl.

The term "$C_{3-6}$-cycloalkyl group" may refer to cyclopropyl, cyclobutyl, cyclopentyl or cyclohexyl. The term "$C_{4-6}$-alkylcycloalkyl group" may, for instance, refer to a cyclopropylmethyl, a 1-cyclopropylethyl, a 2-cyclopropylethyl or to a cyclopentylmethyl group. A "$C_{4-6}$-cycloalkylalkyl group" in the general Formula (I) may be represented by inter alia methylcyclopropyl, methylcyclobutyl or methylcyclopentyl groups, which may be (E)- or (Z)-isomers.

The term "alkenyl group" refers to straight chain or branched aliphatic group comprising a carbon-carbon double bound. Thus, the term "$C_{2-6}$-alkenyl group" refers to straight chain or branched alkenyl group having between 2 and 6 carbon atoms. Examples of $C_{2-6}$-alkenyl groups include are not limited to vinyl, allyl, methallyl, 1-propenyl and 5-hexenyl groups. In one preferred embodiment of the present invention, "$C_{2-6}$-alkenyl group" is a vinyl or an allyl group.

The term "alkynyl group" refers to straight chain or branched aliphatic group comprising a carbon-carbon triple bound. Thus, the term "$C_{2-6}$-alkynyl group" refers to straight chain or branched alkynyl group having between 2 and 6 carbon atoms. Examples of $C_{2-6}$-alkynyl groups include are not limited to ethynyl, 1-propynyl, 2-propynyl, 1-butynyl, 2-butynyl, 3-butynyl, 1-pentynyl, 2-pentynyl, 3-pentynyl, 4-pentynyl and 1-hexynyl. In one preferred embodiment of the present invention, "$C_{2-6}$-alkynyl group" is ethynyl, 1-propynyl or 2-propynyl group.

The term "alkadienyl group" refers to straight chain or branched aliphatic group comprising two carbon-carbon double bounds. Thus, the term "$C_{4-6}$-alkadienyl group" refers to straight chain or branched alkadienyl group having between 4 and 6 carbon atoms. Examples of $C_{4-6}$-alkadienyl groups include are not limited to 1,3-butadienyl, 1,3-pentadienyl or 2,4-pentadienyl.

The term "alkynenyl group" refers to traight chain or branched aliphatic group comprising two carbon-carbon double bounds. Thus, the term "$C_{4-6}$-alkynenyl group" refers to straight chain or branched alkynenyl group having between 4 and 6 carbon atoms. Examples of $C_{4-6}$-alkynenyl groups include are not limited to but-1-en-3-inyl, pent-1-en-3-inyl or hex-1-en-3-inyl.

The aliphatic group such as alkyl group, e.g. the $C_{1-6}$-alkyl group may be optionally substituted with one or more halogen atoms. Thus, for instance, the corresponding substituent may be a perfluorated alkyl group such as, for instance, trifluoromethyl, pentafluoroethyl or n-heptafluoropropyl. In a particularly preferred embodiment of the present invention, the term "$C_{1-6}$-aliphatic group optionally substituted with one or more halogen atoms" refers to a trifluoromethyl group.

In one preferred embodiment, the present invention provides the compound of general Formula (I) or a salt thereof wherein $R^1$ is a halogen atom, or a $C_{1-6}$ alkyl group optionally substituted with one or more halogen atoms, $R^2$ is a $C_{2-6}$-alkyl group optionally substituted with one or more halogen atoms, $Y^2$, $Z^1$ and $Z^2$ are represented by =CH— and $Y^2$ is represented by =N—, and W is represented by —O—.

In a further preferred embodiment, the present invention provides the compound of general Formula (I) or a salt thereof, wherein $R^1$ is a halogen atom, or a $C_{1-6}$-alkyl group optionally substituted with one or more halogen atoms, $R^2$ is a $C_{2-6}$-alkyl group optionally substituted with one or more halogen atoms, $Y^2$, $Z^1$ and $Y^2$ are represented by =CH— and $Z^2$ is represented by =N—, and W is represented by —O—.

In a further preferred embodiment, the compound of the present invention is represented by the general Formula (I) wherein $R^1$ is a halogen atom, or a $C_{1-6}$-alkyl group optionally substituted with one or more halogen atoms, $R^2$ is a $C_{2-6}$-alkyl group optionally substituted with one or more halogen atoms, $Y^1$, $Z^1$, $Y^2$ and $Z^2$ are represented by =CH—, and W is represented by —O—.

In yet a further preferred embodiment, the compound of the present invention is represented by the general Formula (I) wherein $R^1$ is a chlorine atom, or a $C_{1-3}$-alkyl group optionally substituted with one or more halogen atoms, $R^2$ is a $C_{2-4}$-alkyl group optionally substituted with one or more halogen atoms, $Y^3$ is represented by —CH—, and W is represented by —O—.

In a particularly preferred embodiment, the compound of the present invention is represented by the general Formula (I) wherein $R^1$ is a fluorine atom, a chlorine atom, or a methyl group,

$R^2$ is an ethyl group or a n-propyl group,

X is represented by —O—, —S—, or —CH$_2$—,

$Y^1$, $Z^1$, $Y^2$, $Z^2$ and $Y^3$ are represented by —CH—, and

W is represented by —O—.

As will be appreciated by those skilled in the art, the structural moiety in the general Formula (I) may have a 1,4-substitution pattern, a 1,3-substitution pattern or a 1,2-substitution pattern. In one embodiment of the present invention, said moiety has a 1,3-substitution pattern. Thus, the compound of the present invention is represented by the Formula (Ia)

(Ia)

In yet another embodiment of the present invention, the corresponding structural moiety has a 1,4-substitution pattern. Thus, the compound of the present invention is represented by the Formula (Ib)

(Ib)

In a particularly preferred embodiment of the present invention, the structural fragment in the general Formula (I) may be selected from the group comprising the following substituents:

Preferably, the structural moiety in the general Formula (I) is represented by a structure selected from the group comprising the following structural elements:

Examples of particularly preferred compounds of the present invention include but are not limited to the following compounds:

(1)

(2)

(3)

(4)

(5)

(6)

(7)

(8)

A further aspect of the present invention relates to use of the compounds of Formula (I) for therapy and/or prophylaxis of degenerative diseases of nervous system. The corresponding degenerative diseases of nervous system may be selected from the group consisting of senile dementia, Alzheimer's disease, Pick's disease, Huntington's chorea, cerebrocerebellar degeneration, amaurotic family idiocy (neuronal lipidoses), leukodystrophy, familial myoclonus epilepsy, and Wilson's disease (hepatolenticular degeneration, Westphal-Strumpell pseudosclerosis).

In a further embodiment, the degenerative diseases of the nervous system may be selected from the group consisting of paralysis agitans (Parkinson's disease), dystonia musculorum deformans (torsion dystonia), Hallervorden-Spatz disease and other restricted dyskinesias, familial tremor and spasmodic torticollis, cerebellar degenerations and spinocerebellar degenerations (Friedreich's ataxia, Marie's hereditary ataxia), amyotrophic lateral sclerosis, progressive muscular atrophy, progressive bulbar palsy, primary lateral sclerosis, infantile muscular atrophy (Werdnig-Hoffmann disease), other forms of familial progressive muscular atrophy (including Wohlfart-Kugelberg-Welander syndrome), cachexia and sarcopenia, hereditary spastic paraplegia, progressive neural muscular atrophy, peroneal muscular atrophy (Charcot-Marie-Tooth), hypertrophic interstitial neuropathy (Dejerine-Sottas), miscellaneous forms of chronic progressive neuropathy, hereditary optic atrophy (Leber's disease), age-related macular degeneration and pigmentary degeneration of the retina (retinitis pigmentosa).

Yet, in a further embodiment the degenerative diseases of the nervous system are selected from the group consisting of depression and schizophrenia.

In a particularly preferred embodiment of the present invention, the compounds of the general Formula (I) are used in the treatment and/or prophylaxis of Alzheimer's disease.

The compounds of Formula (I) can be prepared essentially as described by Fernandez et al., 2002, Tetrahedron Letters 43, 4741-4745; Starchenkov et al., Chemistry of Heterocyclic Compounds 1997, 33(19), 1219-1233; and Khim. Geterotskil, Soedin., 1997, 1402-1416.

The compounds of the invention include pharmaceutically acceptable salts, amides, and prodrugs therof, including but not limited to carboxylate salts, amino acid addition salts, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobsonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like, (See, for example, Berge S. M, et al., "Pharmaceutical Salts," J. Pharm, Sci., 1977; 66:1-19 which is incorporated herein by reference.)

A further aspect of the present invention includes pharmaceutical compositions comprising a therapeutically effective amount of one or more compounds of the invention disclosed above, associated with a pharmaceutically acceptable carrier. For administration, the compounds are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Examples of pharmaceutically acceptable, non-toxic amides of the compounds of this invention include amides derived from secondary amines. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated, by reference.

The compounds of the present invention can be administered individually or in combination, usually in the form of a pharmaceutical composition. Such compositions are prepared in a manner well known in the pharmaceutical art and comprise at least one active compound.

Accordingly, a further aspect of the present invention includes pharmaceutical compositions comprising as one or more compounds of the invention disclosed above, associated with a pharmaceutically acceptable carrier. For administration, the compounds are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Preferred embodiments of the present invention include the following (1) to (15):

(1) A compound of general Formula (II)

(II)

or a salt thereof, whereby $R^1$ is a hydrogen atom, a halogen atom or a $C_{1-6}$-alkyl group optionally substituted with one or more halogen atoms, $R^2$ is a $C_{1-6}$-aliphatic group optionally substituted with one or more halogen atoms, X is represented by —O—, —S—, —S(O)—, —S(O)$_2$—, —NH—, —C(O)—, or —CH$_2$—, $Y^1$, $Z^1$, $Y^2$, $Z^2$ and $Y^3$ are independently represented by —CH— or —N—, and W is represented by —O—, —S—, —NH—, or —C(O)—.

(2) The compound of general Formula according to (1) or a salt thereof, whereby $R^1$ is a halogen atom, or a $C_{1-6}$-alkyl group optionally substituted with one or more halogen atoms, $R^2$ is a $C_{2-6}$ alkyl group optionally substituted with one or more halogen atoms, $Y^2$, $Z^1$ and $Z^2$ are represented by =CH— and $Y^2$ is represented by =N—, and W is represented by —O—.

(3) The compound of general Formula (II) according to (1) or a salt thereof, whereby $R^1$ is a halogen atom, or a $C_{1-6}$-alkyl group optionally substituted with one or more halogen atoms, $R^2$ is a $C_{2-6}$-alkyl group optionally substituted with one more halogen atoms, $Y^2$, $Z^1$ and $Y^2$ are represented by =CH— and $Z^2$ is represented by =N— and W is represented by —O—.

(4) The compound of general Formula (II) according to (1) or a salt thereof, whereby $R^1$ is a halogen atom, or a $C_{1-6}$-alkyl group optionally substituted with one or more halogen atoms, $R^2$ is a $C_{2-6}$-alkyl group optionally substituted with one or more halogen atoms, $Y^1$, $Z^1$, $Y^2$ and $Z^2$ are represented by =CH— and W is represented by —O—.

(5) The compound of general Formula (II) car a salt thereof according to any of (1) to (4), whereby

$R^1$ is a chlorine atom, or a $C_{1-3}$-alkyl group options substituted with one or more halogen atoms, $R^2$ is a $C_{2-4}$-alkyl group optionally substituted with one or more halogen atoms, $Y^3$ is represented by —CH—, and

W is represented by —O—.

(6) The compound of general Formula (II) or a salt thereof according to any of (1) to (5), whereby
the compound is represented by the Formula (IIa):

(IIa)

(7) The compound of general Formula (II) or a salt thereof according to any of (1) to (5), whereby the compound is represented by the Formula (IIb):

(IIb)

(8) The compound of general Formula (II) or a salt thereof according to (6) or (7), whereby
$R^1$ is a fluorine atom, a chlorine atom, or a methyl group,
$R^2$ is an ethyl group or a n-propyl group,
X is represented by —O—, —S—, or —CH$_2$—,
$Y^1$, $Z^1$, $Y^2$, $Z^2$ and $Y^3$ are represented by —CH—, and
W is represented by —O—.

(9) The compound of general Formula (II) according to any of (1) to (8) or a salt thereof for use in the treatment of a human or animal body.

(10) The compound of general Formula (II) according to any of (1) to (8) or a salt thereof for use in the treatment or prophylaxis of a degenerative disease of the nervous system.

(11) The compound of general Formula (II) according to any of (1) to (8) or a salt thereof for use according to (10), whereby the degenerative disease of the nervous system is selected from the group consisting of senile dementia, Alzheimer's disease, Pick's disease, Huntington's chorea, cerebrocerebellar degeneration, amaurotic family idiocy (neuronal lipidoses), leukodystrophy, familial myoclonus epilepsy, and Wilson's disease (hepatolenticular degeneration, Westphal-Strumpell pseudosclerosis).

(12) The compound of general Formula (II) according to any of (1) to (8) or a salt thereof for use according to (10), whereby the degenerative disease of the nervous system is selected from the group consisting of paralysis agitans (Parkinson's disease), dystonia musculorum deformans (torsion dystonia), Hallervorden-Spatz disease and other restricted dyskinesias, familial tremor and spasmodic torticollis, cerebellar degenerations and spinocerebellar degenerations (Friedreich's ataxia, Marie's hereditary ataxia), amyotrophic lateral sclerosis, progressive muscular atrophy, cachexia and sarcopenia, progressive bulbar palsy, primary lateral sclerosis, infantile muscular atrophy (Werdnig-Hoffmann disease), other forms of familial progressive muscular atrophy (including Wohlfart-Kugelberg-Welander syndrome), hereditary spastic paraplegia, progressive neural muscular atrophy, peroneal muscular atrophy (Charcot-Marie-Tooth), hypertrophic interstitial neuropathy (Dejerine-Sottas), miscellaneous forms of chronic progressive neuropathy, hereditary optic atrophy (Leber's disease), age-related macular degeneration and pigmentary degeneration of the retina (retinitis pigmentosa).

(13) The compound of general Formula (II) according to any of (1) to (8) or a salt thereof for use according to (10), whereby the degenerative disease of the nervous system is selected from the group consisting of depression and schizophrenia.

(14) A pharmaceutical composition comprising a therapeutically effective amount of the compound of general Formula (II) according to any of (1) to (8) or of a salt thereof as active ingredient.

(15) The pharmaceutical composition according to (14), whereby said pharmaceutical composition is an oral dosage form.

The following examples are intended for the sole purpose of illustrating the present invention.

EXAMPLES

Example 1

Binding Assay 1.1 Material s and Methods
p38

To examine the inhibition of the compounds 1 to 12, in vitro kinase assays were performed. Purified recombinant activated p38alpha (10 nM)(ProQinase) was preincubated 10 minutes at 30° C. with the compound of interest at concentrations between 1 and 100 µM in duplicate in a final volume of 30 µl of kinase buffer (Hepes 60 mM pH 7.5, MgCl$_2$ 3 mM, MnCl$_2$ 3 mM, sodium orthovanadate 3 µM, DTT 1.2 mM). After preincubation, peptide substrate (SignalChem #P03-58) and ATP were added to a final concentration of 10 µM and 100 µM respectively, and then incubated 40 minutes at 30° C. for the kinase reaction. Phosphorylation was analysed with ADP-Glo™ (Promega

V9101) and emitted luminescence was measured with BMG Fluostar microplate reader.

JNK

To examine the inhibition of the compounds 1 to 12, in vitro kinase assays were performed. Purified recombinant activated JNK (10 nM) (ProQinase) was preincubated 10 minutes at 30° C. with the compound of interest at concentrations between 1 and 100 μM in duplicate in a final volume of 30 μl of kinase buffer (Hepes 60 mM pH 7.5, $MgCl_2$ 3 mM, $MnCl_2$ 3 mM, sodium orthovanadate 3 μM, DTT 1.2 mM). After preincubation, peptide substrate (SignalChem #P03-58) and ATP were added to a final concentration of 10 μM and 100 μM respectively, and then incubated 40 minutes at 30° C. for the kinase reaction. Phosphorylation was analyzed with ADP-Glo™ (Promega #V9101) and emitted luminescence was measured with BMG Fluostar microplate reader.

Thp1-Inhibition of TNF-α Secretion by a Human Monocytic Cell Line, THP-1

THP-1 cells, growing in log phase, were collected by centrifugation and resuspended in RPMI 1640 (Sigma Aldrich), to a final cell concentration of 2×106 cells/ml. Cells were plated into 24-well plates (BD Biosciences). Dilutions of compounds in dimethyl sulfoxide (DMSO) were added to the culture to a final concentration M. The final DMSO concentration was 0.5%. The cells ranging from 0.1 to 50 suspensions were preincubated with compounds for 1 h at 37° C. in a 5% $CO_2$ humidified atmosphere before the addition of LPS (Sigma Aldrich, L2654) to a g/ml. After that, cells were incubated for 3 h followed final concentration of 2° C. by centrifugation to pellet cells. Cell supernatants were stored at 4° C. until human analysis for TNF-α content. TNF-α levels were determined by ELISA (TNF Biotrak, GE Healthcare) following the manufacturer's directions. The percentage inhibition was calculated for each compound concentration tested, and the $IC_{50}$ was calculated for each compound.

p38/JNK Inhibitors Protect From Activated THP-1 Toxic Supernatant in SHSY5Y Cells SH-SY5Y cell line was expanded and maintained in DMEM with 10% FBS, 2 mM glutamine and antibiotics. Cells were differentiated as previously published (Gimenez-Cassina et al; J. Neurosci. Res; 2006). Briefly, $7×10^3$ cells/$cm^2$ were seeded onto Matrigel Basement-coated culture 24-well plates and allowed to attach overnight. Cell were then exposed to 10 uM retinoic acid for 5 days. Subsequently, the cells were cultured in Neurobasal medium, with B27, 2 mM GlutamaxI, 2 mM dbAMPc, 20 mM KCl, 50 ng/ml hBDNF and antibiotics for an additional 5 days.

In parallel, human monocytic THP-1 cells were seeded in 24-well plates ($2×10^6$ cells/ml) in Neurobasal medium without serum and incubated for 24 h in the presence or absence of stimulants LPS (1 μg/ml) and IFNα (333 U/ml). After incubation, cultures were centrifuged and supernatants were transferred to differentiated SH-SY5Y cells. The cells were then incubated for an additional 72 h in the presence or absence of inhibitors. After treatment, viability of cells was evaluated by Cell Titer Glo kit (Promega) and luminescence was measured with a BMG Fluostar microplate reader. Supernatant from nonstimulated THP-1 cells was used as high control.

1.2. Results

The assays were carried out at 10 μM and at 1 μM. The collected results are summarized in Tables 1 and 2 below.

TABLE 1

% of inhibition at 10 μM (for neurons is % of rescue)

| | Comp 1 | Comp 2 | Comp 3 | Comp 4 | Comp 5 | Comp 6 | Comp 7 | Comp 8 | Comp 9 | Comp 10 | Comp 11 | Comp 12 |
|---|---|---|---|---|---|---|---|---|---|---|---|---|
| p38 | 99% | 87% | 100% | 68% | 100% | 95% | 87% | 64% | 68% | 52% | 105% | 95% |
| JNK | 98% | 91% | 96% | 74% | 97% | 91% | 101% | 55% | 51% | 50% | 74% | 90% |
| THP1 | 74% | 69% | 58% | 41% | 65% | 39% | 33% | 37% | 39% | 31% | 50% | 51% |
| Neurons | 51% | 32% | 42% | 22% | 55% | 37% | 38% | 26% | 43% | 47% | 42% | 35% |

TABLE 2

% of inhibition at 1 μM (for neurons is % of rescue)

| | Comp 1 | Comp 2 | Comp 3 | Comp 4 | Comp 5 | Comp 6 | Comp 7 | Comp 8 | Comp 9 | Comp 10 | Comp 11 | Comp 12 |
|---|---|---|---|---|---|---|---|---|---|---|---|---|
| p38 | 37% | 41% | 23% | 25% | 41% | 32% | 19% | 16% | 23% | 25% | 21% | 15% |
| JNK | 49% | 36% | 31% | 31% | 37% | 35% | 34% | 32% | 26% | 30% | 24% | 24% |
| THP1 | 51% | 42% | 37% | 19% | 44% | 28% | 21% | 17% | 27% | 19% | 30% | 45% |
| Neurons | 33% | 25% | 21% | 11% | 32% | 22% | 18% | 12% | 33% | 33% | 41% | 36% |

Thus, all tested compounds 1 to 12 acted as efficient inhibitors of p38 and JNK MAP kinases.

Example 2

Single Dose Intraperioneal and Intravenous Blood Brain Barrier Permeability Study in Male Sprague Dawley Rat The objective of these tests was to determine the plasma and brain concentration of the compound 1 in male Sprague Dawley rat after single intraperioneal (i.p.) and intravenous (i.v.) administration.

2.1 Experimental Procedure

The design of the experiments is summarised in Table 3 below:

TABLE 3

Design of the experiments

| Group | Test compound | Dose (mg/kg) | Dose Volume (mL/Kg) | Dose conc. (mg/mL) | Route | Number of animals | Sample collection time points (h) |
|---|---|---|---|---|---|---|---|
| 1 | 1 | 10 | 2 | 5 | i.p. | 3 | 2 |
| 2 | 1 | 10 | 2 | 5 | i.v. | 3 | 2 |

2.2. Test Compound Administration

The compound 1 was administered intravenously (i.v.) through tail vein and intraperitoneally (i.p.) in abdominal cavity. After dosing of each animal, the time was documented. All animals were observed for any abnormal behavioural signs exhibited after drug administration throughout the study duration.

Formulation Details

Weight of the compound 1: 30.14 mg

Formulation vehicle: 20 Vol.-% Cremophore, 10 Vol.-% ethanol, 70 Vol.-% normal saline Volume of formulation vehicle: 6.028 ml 2.3. Bioanalysis Study Design Bioanalysis was performed using fit-for-purpose LC-MS/MS method for the quantification of test compounds in plasma samples and brain homogenate. The method was validated for calibration curve consisted of nine non-zero calibration standards along with a double blank and zero standard samples. Study samples were analysed along with two sets of quality control samples (6 QC samples; low, medium and high QC sample).

2.4. Sample Collection Details-Blood

Anticoagulant: Lithium Heparin tubes

Collection Site: Blood:—Cannulated Jugular vein

Sample Size: Approximately 0.25-0.30 ml blood

Sample Process: Blood samples were placed on ice prior to centrifugation and centrifuged within 15 min at 5000 rpm for 10 min at 4° C.

Sample Storage: CondPlasma samples promptly stored at −80±10° C. until bioanalysis 2.5. Sample Collection Details-Brain Process of Sample Collection Immediately after blood withdrawal, in situ brain perfusion was performed using chilled saline. The chest of the rat was exposed, the abdominal aorta was clamped and both jugular veins were cut. Intra-cardial perfusion was performed through an insertion in the left ventricle. Perfusion of each rat was followed by exanguination for brain collection. The skin over the cranium was incised and deflected. The head was flexed and a cut was made through the muscles and the spinal cord at the junction of the foreman magnum and atlas vertebra. A circumferential incision was carefully made in the cranium using a bone cutter. The roof of the cranium was lifted off to expose the meninges and brain. The meninges were removed carefully. Then holding the head with the nose pointing upward, the anterior part of the brain was lifted to separate the brain. Separated brain was immediately weighed and frozen at −80±10° C. until homogenization.

Sample Storage Condition

Brain samples were promptly stored at −80±10° C. until bioanalysis.

Brain Homogenization

Brain samples were thawed on ice. An appropriate volume of ice cold homogenizing media (Normal Saline) was added. Brain samples were homogenized on ice with the Polytron® homogenizer and volume was adjusted with homogenizing media to achieve 1 g of brain per 5 ml of homogenate. After homogenization, the brain homogenate were immediately frozen at −80° C. until analysis.

2.6 Results

The results of the analysis are summarised in Tables 4 and 5 below:

TABLE 4

Concentration in rat plasma and brain homogenate i.v. at 2 h

| Time (h) | R1 | R2 | R3 | Mean | Std Dev | % CV |
|---|---|---|---|---|---|---|
| Plasma (ng/mL) | 162.96 | 293.38 | 156.26 | 204.20 | 77.30 | 37.85 |
| Brain Homogenate (ng/g) | 322.70 | 394.80 | 439.45 | 385.65 | 58.91 | 15.28 |

TABLE 5

Concentration in rat plasma and brain homogenate i.p. at 2 h

| Time (h) | R1 | R2 | R3 | Mean | Std Dev | % CV |
|---|---|---|---|---|---|---|
| Plasma (ng/mL) | 123.03 | 63.64 | 87.75 | 91.47 | 29.87 | 32.65 |
| Brain Homogenate (ng/g) | 49.10 | 31.30 | 44.55 | 41.65 | 9.25 | 22.20 |

Thus, the above results illustrate that the compound 1 has an excellent blood-brain permeability. Accordingly, this compound as well as other structurally related compounds of the present invention are capable of reaching p38α and JNK MAP kinases located in the brain and in nervous tissues.

Example 3

Analysis of the Protective Properties of a Test Compound 1 Against Aβ$_{25-35}$ Amyloid Peptide-Induced Toxicity in Vivo in Rats The purpose of the study was to determine whether the test compound 1 can alleviate the pathology produced in rats by the acute intracerebroventricular (i.c.v) injection of an oligomeric Aβ25-35 peptide preparation.

The compound efficacy was evaluated 7 days after the peptide administration, on:
- the attenuation of the Aβ$_{25-35}$-induced learning deficits (recognition long-term memory: novel object recognition);
- the attenuation of the Aβ$_{25-35}$-induced Aβ$^{1-42}$ accumulation in the rat hippocampus.

One administration procedure was examined: the compound 1 (10 mg/kg) administered intraveinously (i.v.) once a day during 9 days.

3.2 Protocols and Materials

Animals and Treatment Groups 36 male Sprague Dawley RjHan:SD rats (230-260 g) were used. 3 animal groups with n=12 per group were constituted in the following manner:

|  | Number |
|---|---|
| 1. Sc.Aβ + vehicle (i.v.) | 12 |
| 2. Aβ$_{25-35}$ + vehicle (i.v.) | 12 |
| 3. Aβ$_{25-35}$ + compound 1 (10 mg/kg i.v.) | 12 |
| Total | 36 |

On day 0, Aβ$_{25-35}$ (oligomeric, 9 nmol) or scrambled Aβ$_{25-35}$ peptide control (Sc.Aβ, 9 nmol) was administered i.c.v. at 09:00 am.

Compound 1 or vehicle, was administered i.v. once-a-day between day 0 and day 9, at 09:30 am.

On day 8 and 9, the recognition long-term memory of the animals was assessed using the novel object recognition (NOR) procedure. Habituation (session without object) was performed on day 7.

On day 10, all animals were sacrificed, the frontal cortex and hippocampi dissected out. One hippocampus was used for the ELISA analyses of Aβ$_{1-42}$ content.

Formulations

All solutions were freshly prepared before each administration. The vehicle was Ethanol 5% (Fluka), Cremophor (ref. C-5135, Batch 32H0925, Sigma-Aldrich) 20% in physiological saline and administered in 2.5 mg/ml. Treatment groups were prepared as follows:
Group 1, 2: vehicle solution (distilled water)
Group 3: compound 1 at 2.5 mg/ml.
Amyloid-β Peptides
Aβ$_{25-35}$:
Denomination: amyloid-β protein (25-35), human, mouse, rat
CAS: 131602-53-4
Supplier: Polypeptides (France)
Reference: SC489
Batch: AW13285A
Molecular Weight: 1060.28
Storage Temp: −20° C.
Appearance: white powder Sc.Aβ:
Denomination: scrambled amyloid-β protein (25-35), human, mouse, rat
CAS: NA
Supplier: Polypeptides (France)
Reference: SC942
Batch: AW13157A
Molecular Weight: 1060.26
Storage Temp: −20° C.
Appearance: white powder Peptides Preparation and Injection Rats received a bilateral i.c.v. injection of Aβ$_{25-35}$ peptide (2×5 nmol/side), or Sc.Aβ peptide (2×5 nmol/side), using the stereotaxic method. Animals were anesthetized with an intramuscular injection of 0.2 ml of a mixture of ketamine hydrochloride (80 mg/kg b.w.) and xylazine (10 mg/kg b.w.). They were then fixed on a stereotaxic frame (David Kopf), their skull exposed, cleaned with H$_2$O$_2$ and holes drilled at the stereotaxic coordinates AP: −1 mm and L: ±1.5 mm. They were then bilaterally injected (2×5 μl) into the lateral ventricles at V: −3.5 mm. The skin was then sutured and cleaned with betadine 10% solution (Asta Medica).

The homogeneous oligomeric preparation of the Aβ$_{25-35}$ peptide was performed according to the AMYLGEN's owned procedure.

Administration of the Test Compound and/or the Vehicle Solution
Route: i.v., into the tail vein
Frequency: once daily at 10:00 am.
Treatment length: 9 days, from day 0 (immediately after the peptide injection) to day 8 (2 h before the NOR session 2).

Animals

Male Sprague Dawley rats, weighing 230-260 g, from Janvier (Saint Berthevin, France), were kept for housing and experiments took place within the animal facility building of the University of Montpellier 2 (CECEMA, Office of Veterinary Services agreement # B-34-172-23). Animals were housed in groups of 3 individuals with access to food and water ad libitum, except during behavioural experiments. They were kept in a temperature and humidity controlled animal facility on a 12 h/12 h light/dark cycle (lights off at 07:00 pm). Rats were numbered by marking their tails using permanent markers. All animal procedures were conducted in strict adherence to the EU Directive 86/609, modified by the decrees 87-848 and 2001-464.

Randomization of the Treatments and Animals

Animal treatments were randomized. All drug injections were performed once-a-day by a personnel not involved in the behavioural experiments.

Mortality

Acute or delayed mortality was checked every day. One animal deceased after the stereotaxic surgery. No animal deceased during the i.v. treatment period.

3.3 Behavioural and Biochemical Analyses

Novel Object Recognition

Session 1: on day 7 after peptide injection, rats were placed individually in a squared open-field (100 cm×100 cm×50 cm high) made in white plexiglas with a floor equipped with infrared light emitting diodes. Rats were habituated to the open-field during a 10-min duration session.

Session 2: on day 8 after peptide injection, two identical objects (50 ml plastic vials with caps) were placed at defined positions (at ¼ and ¾ of one diagonal of the open-field). Each rat was placed in the open-field and the exploratory activity recorded during a 10-min duration session. The activity was analyzed using the Nosetrack® protocol (Viewpoint), in terms of number of contact with objects and duration of contacts. The open-field and objects were cleaned using a 50 ethanol solution between two experiments.

Session 3: on day 9, the object in position #1 was replaced by a novel one (a soft plastic chair feet protection) differing in color shape and texture from the familiar object. Each rat was placed again in the open-field and the exploratory activity recorded during a 10-min duration session. The activity was analyzed similarly. The preferential exploration index was calculated as the ratio of the number (or duration) of contacts with the object in position #1 over the total number for duration) of contacts with the two objects.

Animals showing no contact with one object or less than 10 contacts with one object during session 2 were considered as not satisfactorily exploring each identical object and discarded from the calculations. Five animals were discarded accordingly. Attrition was therefore 11.1%, which remains moderate in this procedure.

Sacrifice of the Animals and Brain Sampling

At the end of the behaviour, all rats were sacrificed by decapitation and frontal cortex and both hippocampi were rapidly removed, weighed and kept in liquid nitrogen until assayed.

ELISA Assays

Samples were prepared from one hippocampus tissues of each rat per group and homogenized in an extraction buffer specific to the commercial ELISA assay kits.

Kits used:

$A\beta_{1-42}$: Supplier USCN, Ref. SEA946Ra, Batch number L140311213.

After thawing, the hippocampus were homogenized in 50 mM Tris-150 mM NaCl buffer, pH 7.5, and sonicated for 20 s. After centrifugation (16,100 g for 15 min, 4° C.), supernatants were used for $A\beta_{1-42}$ ELISA assay according to the manufacturer instructions. Absorbance was read at 450 nm and sample concentration was calculated using the standard curve. Results will be expressed in pg of $A\beta_{1-42}$ per mg of tissue. All samples were assayed in duplicates.

Measure of Protein Concentration

Quantification of proteins was performed with the Pierce BCA (bicinchoninic acid) protein assay kit (Pierce, Ref #23227) to evaluate extraction performance and allow normalization. Standard solutions were prepared by dilution in series from a bovine serum albumin stock solution at 2 mg/ml in 0.9% NaCl with sodium azide (Ref. 23209, Pierce), as follows:

Solution A: 2 mg/ml, 75 µl stock solution.
Solution B: 1 mg/ml, 50 µl of solution A+50 µl PBS
Solution C: 0.5 mg/ml, 50 µl of solution B+50 µl PBS
Solution D: 0.25 mg/ml, 50 µl of solution C+50 µl PBS
Solution E: 0.125 mg/ml, 50 µl of solution D+50 µl PBS
Solution F: 0.05 mg/ml, 10 µl of solution C+90 µl PB
Solution G: 0.025 mg/ml, 50 µl of solution F+50 µl PBS
Solution H: 100 µl PBS (0 mg/ml)

10 µl of standard and samples were added in duplicates on a 96 well plate (samples will be diluted 5× in PBS). Working reagent was added, 200 µl/well (Reagent A+Reagent B to ratio 50/1), then mixed 30 s and before incubating the plate at 37° C. for 30 min. The absorbance was measured at 562 nm.

The total protein concentrations were then calculated from standard curve dilutions and served to normalize Elisa.

Statistical Analyses

All values were expressed as mean±S.E.M. Statistical analyses were performed on the different conditions using one-way ANOVA (F value), followed by the Dunnett's post-hoc multiple comparison test. $p<0.05$ was considered as statistically significant.

Novel object data (contact preference with object #2 or novel object, calculated in terms of number or duration of contact) were expressed as mean±S.E.M. and analysed using a one-way ANOVA and one-sample t-test vs the "no preference" level (50%) for each treatment group.

3.4 Results and Comments

Novel Object Recognition

This procedure is usually a high attrition procedure, since animals must interact with both objects during the two sessions with objects, to be included in the calculations. Animals showing an extreme place bias in exploration of the two identical objects in session 2 ($P_{ref}>90\%$ or $<10\%$) are also discarded. In this study, 4 animals were discarded accordingly, which represent a 11% attrition. They distributed in two of the three experimental groups, suggesting no link with a particular treatment.

The collected experimental results are summarized in the diagrams shown in FIGS. 1a-d. These diagrams illustrate the effect of the compound 1 in rats submitted to the novel object recognition test, 8-9 days after $A\beta_{25-35}$ injection: place preference in term of time spent in the closed arm over time spent in the open arm in (a) and place preference in term of entries into the closed arm over entries into the open arm in (b).

*$p<0.05$, ***$p<0.001$ vs. no preference level (50); one sample t-test; Alk3a12 stands for the group threated with the compound 1.

Object preference in session 2, calculated using contacts to objects (FIG. 1a) or duration of contacts (FIG. 1b) was around 50% for all groups, with the notable exception of the $A\beta_{25-35}$/compound 1-treated group that was significantly higher than 50%. Indeed, two animals showed very high (>65%) preference for the object #2.

Figure 1A:
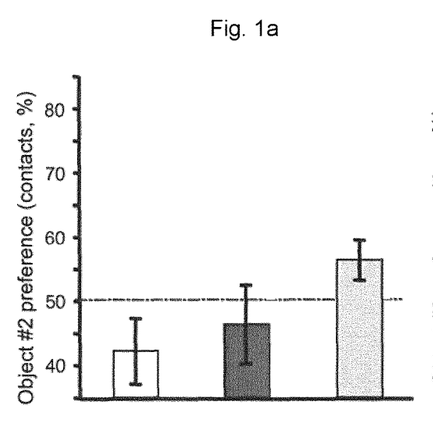
FIGS. 1a-1d Alleviation of the pathology produced in rats by the acute intracerebrovesicular injection of an oligomeric Aβ$_{25-35}$ peptide preparation by the compound 1.
Figure 1B:
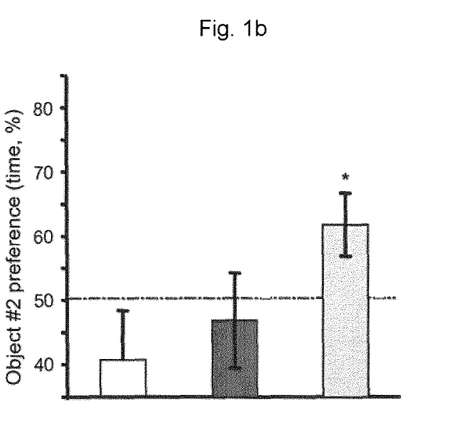
Figure 1C:
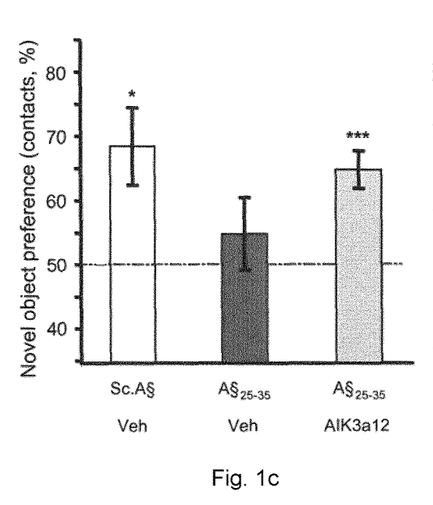
Figure 1D:
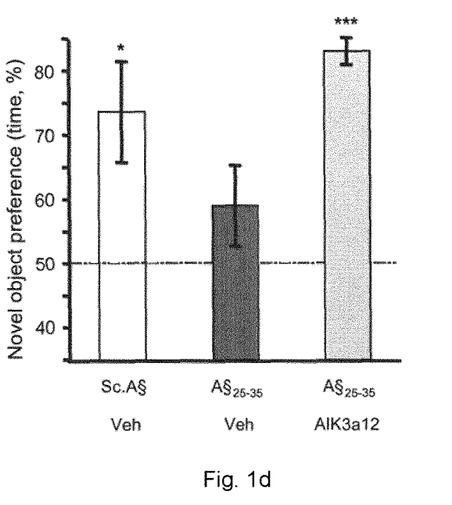

Novel object preference in session 3 showed that Sc.Aβ/Veh-treated animals expressed a significant preference for the novel object, both in terms of number of contacts (FIG. 1c) and duration of contact (FIG. 1d). The $A\beta_{25-35}$/Veh-treated animals failed to show any preference for the novel object (FIG. 1c, d).

The compound 1 treatment alleviated the impairments, since both parameters appeared highly significantly different from the 50% level (FIG. 1c, 1d).

Measurement of $A\beta_{1-42}$ Levels by ELISA

The $A\beta_{1-42}$ level in the hippocampus of control Sc.Aβ/Veh-treated rats was estimated about 1.2 pg/mg tissue. The $A\beta_{25-35}$-induced toxicity induced a significant +158% increase in $A\beta_{1-42}$ tissue content (FIG. 2).

Figure 2:
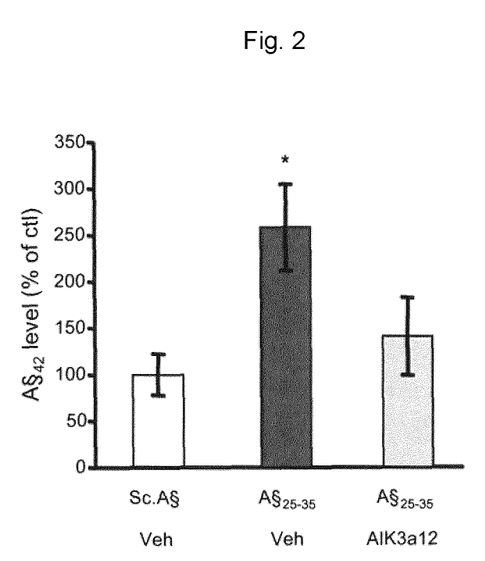
FIG. 2 Decrease of the Aβ$_{1-42}$ level increase in rats as a consequence of administration of the compound 1.

FIG. 2 shows $A\beta_{1-42}$ contents in the rat hippocampus treated with the compound 1, 9 days after $A\beta_{25-35}$ injection.

Veh: vehicle solution. **$p<0.01$ vs. Sc.Aβ/Veh, Dunnett's test;

Alk3a12 stands for the group threated with the compound 1.

The treatment of animals with the compound 1 decreased the $A\beta_{1-42}$ level increase, since the data was not significantly different from the Sc.Aβ/Veh-treated group value (FIG. 2). A high intra-assay variation was noted leading to a marked dispersion of the data.

The invention claimed is:

1. A compound of Formula (I)

(I)

or a salt thereof, wherein

A is benzofuryl, dihydrobenzofuranyl or is represented by the following structure:

$R^1$ is a hydrogen atom, a halogen atom or a $C_{1-6}$-alkyl group optionally substituted with one or more halogen atoms, $R^2$ is a $C_{1-6}$-aliphatic group optionally substituted with one or more halogen atoms, X is represented by —O—, —S—, —S(O)—, —S(O)$_2$—, —NH—, —C(O)—, or —CH$_2$—, $Y^1$, $Z^1$, $Y^2$, $Z^2$ and $Y^3$ are independently represented by —CH— or —N—, and W is represented by —O—, —S—, —NH—, or —C(O).

2. The compound of Formula (I) according to claim 1, wherein the compound is represented by the Formula (II):

(II)

or a salt thereof, wherein $R^1$ is a hydrogen atom, a halogen atom or a $C_{1-6}$-alkyl group optionally substituted with one or more halogen atoms, $R^2$ is a $C_{1-6}$-aliphatic group optionally substituted with one or more halogen atoms, X is represented by —O—, —S—, —S(O)—, —S(O)$_2$—, —NH—, —C(O)—, or —CH$_2$—, $Y^1$, $Z^1$, $Y^2$, $Z^2$ and $Y^3$ are independently represented by —CH— or —N—, and W is represented by —O—, —S—, —NH—, or —C(O)—.

3. The compound of Formula (I) according to claim 1 or a salt thereof, wherein $R^1$ is a halogen atom, or a $C_{1-6}$-alkyl group optionally substituted with one or more halogen atoms, $R^2$ is a $C_{2-6}$-alkyl group optionally substituted with one or more halogen atoms, $Y^2$, $Z^1$ and $Z^2$ are represented by =CH— and $Y^2$ is represented by =N—, and W is represented by —O—.

4. The compound of Formula (I) according to claim 1 or a salt thereof, wherein $R^1$ is a halogen, atom, or a $C_{1-6}$-alkyl group optionally substituted with one or more halogen atoms, $R^2$ is a $C_{2-6}$-alkyl group optionally substituted with one or more halogen atoms, $Y^2$, $Z^1$ and $Y^2$ are represented by =CH— and $Z^2$ is represented by =N—, and W is represented by —O—.

5. The compound of Formula (I) according to claim 1 or a salt thereof, wherein $R^1$ is a halogen atom, or a $C_{1-6}$-alkyl group optionally substituted with one or more halogen atoms, R2 is a $C_{2-6}$-alkyl group optionally substituted with one or more halogen atoms, $Y^1$, $Z^1$, $Y^2$ and $Z^2$ are represented by =CH—, and W is represented by —O—.

6. The compound of Formula (I) or a salt thereof according to claim 1, wherein $R^1$ is a chlorine atom, or a $C_{1-3}$-alkyl group optionally substituted with one or more halogen atoms, $R^2$ is a $C_{2-4}$-alkyl group optionally substituted with one or more halogen atoms, $Y^3$ is represented by —CH—, and

W is represented by —O—.

7. The compound of Formula (I) or a salt thereof according to claim 1, wherein the compound is represented by the Formula (IIa):

(IIa)

8. The compound of Formula (I) or a salt thereof according to claim 1, wherein the compound is represented by the Formula (IIb):

(IIb)

9. The compound of Formula (I) or a salt thereof according to claim 7, wherein
$R^1$ is a fluorine atom, a chlorine atom, or a methyl group,
$R^2$ is an ethyl group or a n-propyl group,
X is represented by —O—, —S—, or —CH$_2$—,
$Y^1$, $Z^1$, $Y^2$, $Z^2$ and $Y^3$ are represented by —CH—, and
W is represented by —O—.

10. A pharmaceutical composition comprising a therapeutically effective amount of the compound of Formula (I)

(I)

or a salt thereof, wherein

A is benzofuryl, dihydrobenzofuranyl or is represented by the following structure:

$R^1$ is a hydrogen atom, a halogen atom or a $C_{1-6}$-alkyl group optionally substituted with one or more halogen atoms, $R^2$ is a $C_{1-6}$-aliphatic group optionally substituted with one or more halogen atoms, X is represented by —O—, —S—, —S(O)—, —S(O)$_2$—, —NH—, —C(O)—, or —CH$_2$—, $Y^1$, $Z^1$, $Y^2$, $Z^2$ and $Y^3$ are independently represented by —CH— or —N—, and W is represented by —O—, —S—, —H—, or —C(O)—;

or a compound according to claim 1 or a salt thereof; as active ingredient.

11. The pharmaceutical composition according to claim 10, wherein said pharmaceutical composition is an oral dosage form.

* * * * *